United States Patent [19]

Hooper et al.

[11] Patent Number: 4,770,040

[45] Date of Patent: Sep. 13, 1988

[54] HUMIDITY SENSOR SYSTEM

[75] Inventors: Edmund M. Hooper, LaSalle; Sidney G. Jones, Howick, both of Canada

[73] Assignee: Flakt Ross, Inc., Canada

[21] Appl. No.: 9,765

[22] Filed: Jan. 29, 1987

[51] Int. Cl.⁴ .............................................. G01N 25/68
[52] U.S. Cl. ......................................... 73/335; 73/338
[58] Field of Search ................... 73/338, 29, 336, 335; 374/16, 21, 28, 27, 109

[56] References Cited

U.S. PATENT DOCUMENTS

| | | | |
|---|---|---|---|
| 1,100,171 | 6/1914 | Brown | 73/29 |
| 3,124,002 | 3/1964 | Pierson et al. | 73/336 |
| 3,253,465 | 5/1966 | Miller | 73/338 |
| 3,603,135 | 9/1971 | Kawaguchi | 73/338 |
| 3,712,140 | 1/1973 | Grasso et al. | 73/338 |
| 3,930,398 | 1/1976 | Levina et al. | 374/21 |
| 4,155,245 | 5/1979 | Coe | 374/21 |
| 4,222,261 | 9/1980 | Leblance et al. | 73/29 |
| 4,481,833 | 11/1984 | Bajek | 73/863.21 |

Primary Examiner—Stewart J. Levy
Assistant Examiner—Hezron E. Williams
Attorney, Agent, or Firm—Connolly & Hutz

[57] ABSTRACT

A humidity sensor system includes a probe in the form of a hollow tubular housing which is attached to a fixed surface. The remote end of the housing has a sensing cap mounted thereto. A liquid coolant supply tube is disposed in the housing and includes a spray nozzle which is located within the cap, but spaced from the inner surface of the cap. The cap is made of a porous material capable of absorbing the liquid coolant sprayed from the nozzle. A temperature detector is mounted to the cap for detecting the temperature change. Also included in the humidity sensor system is a microcomputer which controls the sensor probe, and calculates humidity from the temperature data it generates.

12 Claims, 1 Drawing Sheet

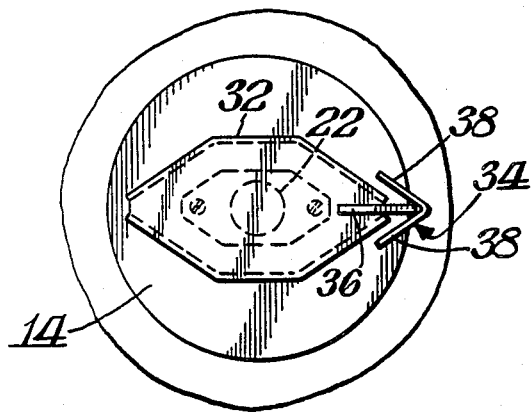
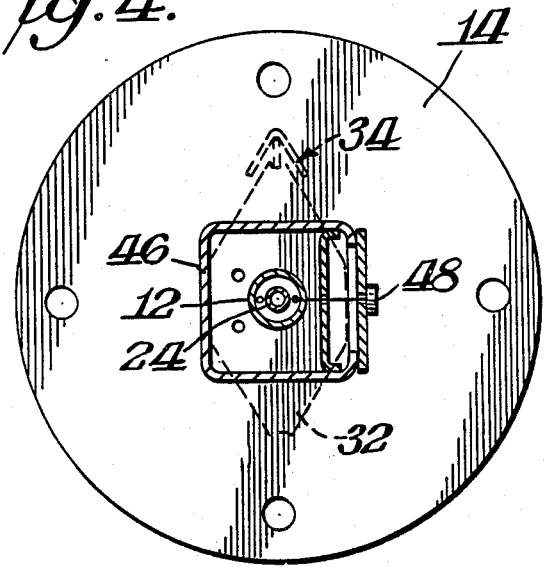
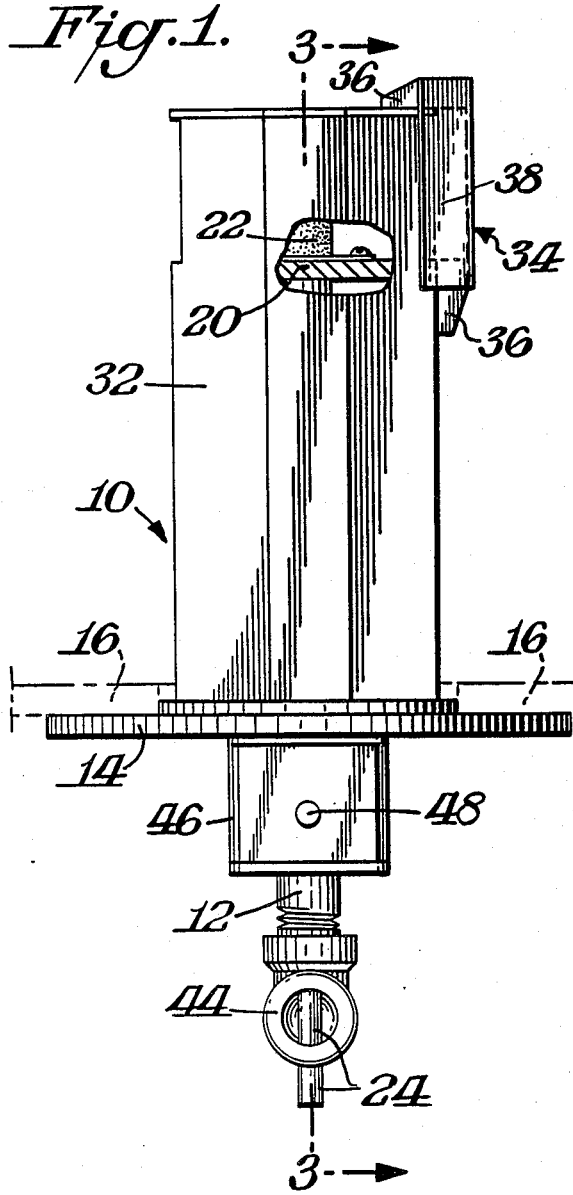
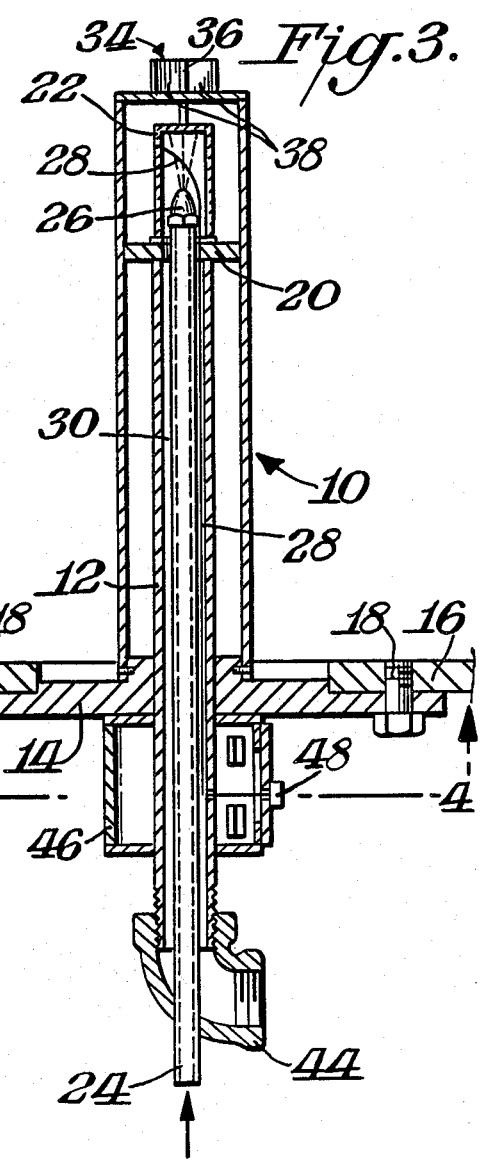

HUMIDITY SENSOR SYSTEM

BACKGROUND OF THE INVENTION

This invention is concerned with the detection of humidity of a hot gas stream. Various machines, such as the Yankee Dryer exist involving gas streams flowing at extremely high temperatures, such as 1000° F. In such high temperature/high humidity environments it would be desirable to determine the humidity of the gas stream for various control purposes. Commonly assigned patent application Ser. No. 847,670, filed Apr. 3, 1986, the details of which are incorporated herein by reference thereto, discloses an approach for determining the humidity. The present invention is directed to variations of the teachings of that application.

SUMMARY OF INVENTION

An objection of this invention is to provide a humidity sensing system which functions as a thermal membrane as a means of detecting temperature drop for determining the wet bulb depression.

A further object of this invention is to determine the humidity by taking into account the time and temperature characteristics in the environment as detected on the probe.

In accordance with this invention the humidity sensing system includes a probe in the form of a hollow tubular housing mounted to a fixed support such as in the process airstream of yankee dryer hood ductwork. A sensing cap is mounted to the remote end of the housing and is made of a porous material. Disposed within the housing is a liquid coolant supply tube which terminates in a spray nozzle for spraying a fine mist of cool liquid such as water to thoroughly soak the porous cap. As the cap absorbs the water there is a temperature drop which is sensed by a temperature detector mounted to the cap. When the temperature of the probe has dropped to a level reasonably below the wet bulb temperature, the spray is turned off, and the probe temperature begins to rise again. Initially the temperature rise is at a rapid rate. The temperature then levels off for a period of time reduces slightly and again rapidly increases. The temperature depression reflects wet bulb temperature.

In a preferred embodiment of this invention a hollow sleeve is mounted around the probe to aid in the cooling action and to reduce the air velocity across the probe. Additionally, a deflector is mounted to the sleeve to prevent solids entrained in the gas stream from dirtying the tip of the probe.

THE DRAWINGS

FIG. 1 is a side elevation view of a humidity sensor in accordance with this invention;

FIG. 2 is a plan view of the humidity sensor shown in FIG. 1;

FIG. 3 is a cross-sectional view taken through FIG. 1 along the line 3—3; and

FIG. 4 is a cross-sectional view taken through FIG. 3 along the line 4—4.

DETAILED DESCRIPTION

Application Ser. No. 847,670, discloses a high temperature humidity sensor system which includes various features utilized by the present invention. The details of that application are incorporated herein by reference thereto and will not be repeated except as are necessary for an understanding of the present invention. Thus, various aspects of that application such as the utilization of a micro-processor with its control functions may likewise be incorporated with the present invention. The present description accordingly will be directed primarily to the features of the system which include the probe mounted to the wall of a yankee dryer hood's ductwork. It is to be understood, of course, that the invention is not intended to be limited to a Yankee Dryer Hood, but may be used in other hot, humid environments where it is desired to determine the humidity.

The system of application Ser. No. 847,670 is based upon the formation of a condensation on the entire ceramic surface of its probe between a pair of electrodes. When moisture forms on the surface a conductive path is formed between the two electrodes which in turn is sensed by a temperature sensor. The temperature sensor detects a sharp fall in the resistance resulting from the moisture or dew forming on the outer surface between the pair of electrodes. The present invention is not based upon the same manner of detecting the humidity. Rather the present invention is based upon determining the humidity by an arrangement which is equivalent to a thermal membrane. A sensor monitors the temperature of the probe to determine when there has been a depression in the temperature plateau following a rapid temperature rise. In this manner, the wet bulb temperature is determined by the time/temperature characteristics.

As shown in FIGS. 1-4 the humidity sensor 10 includes a probe 12 in the form of a hollow, cylindrical, tubular housing having a near end and a remote end. Housing or probe 12 extends through a mounting flange 14 secured to the wall 16 of a Yankee Dryer Hood's Ductwork, by any suitable means such as fasteners 18. The remote end of housing 12 is disposed against a plate 20. A sensing cap 22 is secured to plate 20 in any suitable manner for closing the remote end of housing 12. As later described sensing cap 22 is made of a suitable porous material such as sintered bronze which is capable of absorbing liquid.

Concentrically mounted within housing 12 is a liquid coolant supply tube 24 which terminates at its outer end in a spray nozzle 26 having a spray opening at its tip. A coolant liquid, such as cool water is fed into tube 24 and exits preferably in the form of a fine mist which is sprayed against the inner surface of cap 22.

The hexagonal shape of enclosure for sleeve 32 also functions to cut air turbulence in the same manner that deflector 34 cuts down the velocity of the air in the duct.

Initially, before the spraying action begins, cap 22, because it is mounted in the hot, humid environment, is at an elevated temperature. As cap 22 begins to absorb the water sprayed from nozzle 26 the temperature rapidly decreases. When the temperature of cap 22 is sufficiently below the wet bulb temperature, the water spray is shut off automatically by the microcomputer. The temperature then rises rapidly, levels off, depresses slightly, and then continues on another rapid increase. The depression after the leveling off represents the wet bulb temperature.

As best shown in FIG. 3 the two wires of a thermocouple 28 are mounted on opposite sides of the interior of a cap 22. Conveniently, the wiring for thermocouple 28 is located in the space between housing 12 and tube 24 inside an insulating ceramic jacket 30. Temperature detector 28 functions to monitor the temperature of cap 22 and the monitored information is sent, via a thermocouple plug 48 mounted to chamber 46, to a suitable control station such as a micro-processor which uses the monitored information to calculate and display humidity. The control station may perform other functions as described in application Ser. No. 847,670.

As illustrated in the drawings, sensor 10 includes feature to aid in the cooling of the device. These features include a hollow hexagonal sleeve 32 mounted around housing 12. As illustrated sleeve 32 is provided with a deflector unit 34 in the form of a pair of stems 36 and a pair of converging surfaces 38. Deflector 34 functions to deflect particles in the environment and to cut down on the velocity of air through sleeve 32 and across cap 22. Openings placed in sleeve 32 allow for the correct velocity of air to pass through and across cap 22.

An elbow joint 44 is welded to the near end of housing 12 to provide a water drain. Additionally, a chamber 46 is provided around housing 12 at flange 14. Chamber 46 may house suitable solenoid-operated valves for controlling the flow of water through tube 24 and through a drain or bleed pipe. These solenoid-operated valves may be remotely installed in certain cases.

The invention is based upon the concept of providing a structure, cap 22, which is equivalent to a thermal membrane. At the beginning of the cycle, constant but different temperatures are exposed on either side of the membrane with the average membrane temperature being monitored. The source of the lower constants (inside) temperature is then removed, and the membrane temperature begins to rise. When the temperature of the membrane becomes that of the wet bulb, the membrane absorbs the latent or vaporization heat of the vapor. Although any suitable temperature monitoring sensor can be used the preferred practice of this invention utilizes a J type thermocouple to record the temperature. At the start of operation cap 22 is at the temperature of the air in the dryer duct. Spray nozzle 26 is then turned on and the inside of cap 22, which is in the form of a cylinder having a closed outer end, is blasted with a fine mist of cool water. When cap 22 has been cooled sufficiently below the wet bulb temperature and has become thoroughly soaked the spray is turned off. The hot air of the duct impinges on cap 22 heating it in a classical exponential temperature vs. time curve until cap 22 passes the wet bulb temperature of the air in the duct. At that point the water absorbed in the porous cap starts evaporating and holds the temperature of the cap constant. This is followed by a slight depression in the cap temperature. The lowest point of this depression is taken as the wet bulb temperature. After the water in the cap has sufficiently evaporated then begins a second exponential climb in temperature. Using the wet bulb temperature of the air in the duct as given by the minimum temperature of the cap during the depression stage and the dry bulb temperature of the duct air, plus a program using psychrometric equations, the absolute humidity of the duct air is obtained.

What is claimed is:

1. A humidity sensor system for detecting the wet bulb temperature in a hot, humid environment comprising a probe in the form of a hollow tubular housing having a near end and a remote end, mounting means for attaching said housing at said near end to a fixed support in a generally vertical orientation, a sensing cap mounted to said remote end, a liquid coolant supply tube disposed in said housing, a spray nozzle at the end of said liquid coolant supply tube, said spray nozzle being located within said cap and spaced from the inner surface of said cap so as to spray said inner surface with said liquid coolant which drains from said housing by gravity, said cap being made of a porous metal material capable of absorbing the liquid coolant sprayed from said nozzle under pressure against said inner surface of said cap whereby said cap functions as a thermal membrane, a temperature detector mounted to said cap for detecting the temperature thereof, a sleeve around said probe to reduce the rate of evaporation of water from said probe and to provide a protective covering for said probe, and deflecting means secured to said sleeve.

2. The system of claim 1 wherein said sleeve is closed at its remote end and has a hexagonal cross-section.

3. The system of claim 2 wherein said deflecting means comprises a pair of stems secured to said sleeve, and a pair of diverging plates joined together and secured to said stems at their juncture.

4. The system of claim 1 wherein said cap is made of sintered bronze.

5. The system of claim 4 wherein said cap is cylindrically shaped.

6. The system of claim 1 wherein tubular housing is cylindrically shaped, and said supply tube being cylindrically shaped and concentrically positioned in said housing.

7. The system of claim 6 wherein said temperature detector comprises a thermocouple secured to said cap, and the wiring for said thermocouple extending through the space between the housing and said supply tube.

8. The system of claim 7 including a plate secured across said remote end of said housing, said cap being secured to said plate, and said supply tube extending through said plate.

9. The system of claim 8 wherein said plate is hexagonally shaped, a hexagonal sleeve being mounted around said housing in contact with said plate, and said sleeve having a closed outer end.

10. The system of claim 9 including deflecting means secured to said outer end of said sleeve, said deflecting means comprising a pair of stems secured to and extending outwardly beyond said sleeve, and a pair of diverging plates secured to said stem along their juncture.

11. The system of claim 7 including an elbow secured to said near end of said housing with said mounting means between said elbow and said remote end, and supply tube extending through one end of said elbow and penetrating a wall of said elbow.

12. The system of claim 11 wherein said mounting means comprises a plate-like flange, fasteners extending through said flange for attachment to the fixed support, and said housing extending through said flange.

* * * * *